United States Patent
Patton

[11] Patent Number: 5,965,887
[45] Date of Patent: Oct. 12, 1999

[54] METHOD AND APPARATUS FOR MONITORING MAINTENANCE OF CALIBRATION CONDITION IN RESPIRATORY GAS SPECTROMETER

[75] Inventor: Craig A. Patton, Boulder, Colo.

[73] Assignee: Datex-Ohmeda, Inc., Tewksbury, Mass.

[21] Appl. No.: 08/909,543

[22] Filed: Aug. 12, 1997

[51] Int. Cl.$^6$ ........................................... G01N 21/35
[52] U.S. Cl. ........................ 250/339.09; 250/339.13
[58] Field of Search ........................ 250/339.09, 339.13

[56] References Cited

U.S. PATENT DOCUMENTS

| | | |
|---|---|---|
| 4,459,266 | 7/1984 | Lamoreaux . |
| 4,578,762 | 3/1986 | Wong . |
| 4,692,621 | 9/1987 | Passaro et al. . |
| 4,902,896 | 2/1990 | Fertig, Sr. et al. . |
| 4,955,946 | 9/1990 | Mount et al. . |
| 5,070,245 | 12/1991 | Rantala et al. . |
| 5,081,998 | 1/1992 | Yelderman et al. . |
| 5,095,913 | 3/1992 | Yelderman et al. . |
| 5,129,401 | 7/1992 | Corenman et al. . |
| 5,231,591 | 7/1993 | Flewelling et al. . |
| 5,261,415 | 11/1993 | Dussault . |
| 5,296,706 | 3/1994 | Braig et al. . |
| 5,332,901 | 7/1994 | Eckles et al. ............................ 250/345 |
| 5,464,982 | 11/1995 | Drucker et al. . |
| 5,468,961 | 11/1995 | Gradon et al. . |
| 5,468,962 | 11/1995 | Ohishi et al. . |
| 5,515,859 | 5/1996 | Paz ....................................... 250/339.13 |
| 5,542,285 | 8/1996 | Merilainen et al. . |
| 5,583,339 | 12/1996 | Black et al. ........................ 250/339.13 |

*Primary Examiner*—Constantine Hannaher
*Attorney, Agent, or Firm*—Holme Roberts & Owen L.L.P.

[57] ABSTRACT

A gas spectrometer is provided for the monitoring of the maintenance of desired calibration conditions. The inventive method and apparatus is particularly apt for use in respiratory gas spectrometers. Monitoring may be achieved by first establishing calibration condition values obtained by passing radiation beams through a reference gas chamber and purged, sample gas chambers upon initial calibration. Subsequently, e.g. after the spectrometer has been utilized in the field, corresponding test condition values are obtained by passing radiation beams through the same reference gas chamber and purged, sample gas chambers. Comparisons utilizing the calibrated condition values and test condition values can be made to monitor calibration variances (e.g. variances, in optical pathway conditions and depletion of the radiation source(s) utilized in the gas spectrometer).

18 Claims, 4 Drawing Sheets

METHOD AND APPARATUS FOR MONITORING MAINTENANCE OF CALIBRATION CONDITION IN RESPIRATORY GAS SPECTROMETER

FIELD OF THE INVENTION

This invention relates to gas spectrometers for measuring the concentration of predefined components of a gas sample, and is particularly apt for use in respiratory gas spectrometers that measure the concentration of oxygen, $CO_2$ and/or one or more anesthetic agents in a respiratory gas stream.

BACKGROUND OF THE INVENTION

There are many industrial and medical applications which utilize gas spectrometers to monitor the presence and concentration of one or more predefined components in a gas sample. In this regard, light of a known spectral content may be directed on an optical pathway through a gas sample and the intensity of the transmitted light may be detected at a number of different center-wavelengths. By utilizing known light absorption characteristics of the predefined gas components at the center-wavelengths, the detected light intensities provide a basis to determine, via statistical processing, the concentrations of the predefined components.

As will be appreciated, it is important that initial calibration conditions within a spectrometer be maintained in order to accurately relate measured light intensities to gas component concentrations in use. This is particularly true in respiratory gas spectrometers used to measure the concentration of oxygen, $CO_2$ and/or one or more anesthetic agents such as nitrous oxide, halothane, enflurane, sevoflurane, desflurane and isoflurane in a respiratory gas stream. In such applications, a separate sample stream is typically drawn from a patient respiratory gas assembly and directed into a gas sample chamber that is positioned on the optical pathway between the light source and detector. If there are variations along the optical pathway utilized in the respiratory gas spectrometer which have arisen since calibration (e.g. contamination of the gas sample chamber), such variations may lead to an inaccurate concentration determination.

Further, in order to provide a highly robust respiratory gas spectrometer, it is important that the transmitted radiation from the gas sample chamber yield a sufficiently high signal-to-noise ratio at the detector. This is particularly important when an array of detector elements are simultaneously illuminated by the transmitted radiation. By way of primary concern, the signal-to-noise ratio may unacceptably decrease as the radiation source employed in the spectrometer ages.

SUMMARY OF THE INVENTION

In view of the foregoing, a primary objective of the present invention is to provide a gas spectrometer which is highly responsive for monitoring the maintenance of one or more calibration conditions, and which is particularly apt for respiratory gas analyzers.

More particularly, objectives of the present invention include the provision of a respiratory gas spectrometer which monitors the functionality of the radiation source(s) relied upon in the spectrometer and/or which monitors the maintenance of the calibration condition of one or more optical pathways utilized in the respiratory gas spectrometer.

To achieve such objectives and realize other associated advantages, the inventive gas spectrometer provides for passage of first and second calibration radiation beams on corresponding first and second optical pathways within a calibrated spectrometer (i.e. in a desired, calibration condition). The first and second optical pathways may pass through corresponding first and second gas containment areas, respectively, wherein the containment areas each contain a predetermined gas. Preferably, such predetermined gas will not contain gas components of the type to be measured by the spectrometer, or which would otherwise absorb significant radiation within the operating radiation wavelength range. The intensity of the first and second calibration radiation beams (e.g. as transmitted by the first and second containment areas) is detected to obtain corresponding calibration condition values. Such values may be established upon spectrometer assembly at the factory and may be advantageously stored in a non-volatile memory on-board the gas spectrometer. Subsequently, e.g. after the spectrometer is put into use, the invention provides for the passage of first and second test radiation beams on the first and second pathways, respectively. Again, the first and second optical pathways may pass through the corresponding first and second containment areas of the spectrometer, wherein the first and second containment areas are again provided with a predetermined gas. The intensity of the first and second test radiation beams transmitted through the first and second containment areas is detected to provide corresponding first and second test condition values. In turn, such test condition values may be utilized together with the above-noted calibration condition values to monitor the operating, or test, condition of the spectrometer in relation to the desired calibration condition. In this manner, deviation from the calibrated, or desired, operating condition of a spectrometer can be monitored and appropriate responsive action taken (e.g. servicing).

As will be appreciated, the first and second gas containment areas may comprise a reference gas chamber and sample gas chamber, each chamber having opposing windows which are radiation transmissive. The reference gas chamber may be positioned on the first optical path on which both the first calibration radiation beam and first test radiation beam travel. Similarly, the sample gas chamber may be positioned on the second optical path on which the second calibration radiation beam and second test radiation beam travel.

The described arrangement provides a system for making certain determinations based upon comparisons utilizing the first and second test condition values and the first and second calibration condition values. In particular, by comparing a first ratio of the first and second calibration condition values with a second ratio of the first and second test condition values, a determination can be made as to whether or not there has been a variance in the desired calibration conditions on one of the optical pathways. In this regard, if a comparison between the two ratios indicates a difference greater than a predetermined tolerance value, a user can be alerted that the spectrometer should be serviced. Potential causes for an optical pathway variation may include contamination of the gas sample chamber (e.g., build-up of radiation absorbent material on chamber windows) and misalignment of optical components that may define a given optical pathway. By way of example, gas sample chamber contamination may be indicated when the above-noted second ratio exceeds the first ratio (i.e. since the second test condition value in denominator in second ratio would decrease).

Additionally, determinations can be made regarding the functionality of the radiation source utilized in the spectrometer. That is, by comparing the magnitude of the first calibration condition value to the magnitude of the first test condition value, and by comparing the magnitude of the second calibration condition value to the magnitude of the second test condition value, a determination can be made as to whether the radiation source may be approaching the end of its useful life (e.g., "useful life" being defined by the ability to provide radiation at a power level sufficient to yield the desired single-to-noise ratio at the detector). In this regard, if each of the comparisons reflect a difference greater than a corresponding, predetermined tolerance value(s), a user may be alerted that the radiation source is at or nearing the end of its useful life.

As noted, the present invention is particularly apt for use in respiratory gas spectrometers. In one such embodiment, an infrared radiation source is utilized to provide radiation across a relatively wide wavelength range (e.g., at least about 4–12 microns). An optical chopper is employed to alternately transmit radiation from the source on first and second optical pathways. In the latter regard, separate optical assemblies are provided for collecting and directing radiation on the first and second optical pathways and define corresponding first and second converging optical beams. The reference gas chamber and sample gas chamber are positioned on the optical pathways of the first and second beams, respectively, and transmitted radiation through the chambers is alternately received by a detector assembly. The detector assembly includes a spatial filter (e.g., a linear variable filter) and an array of detector elements for substantially simultaneous detection of transmitted radiation (i.e. alternately from the reference gas and sample gas chambers) at a plurality of center-wavelengths. A processor/controller, memory device and user interface are also included for implementation of the above-noted calibration condition and test condition procedures comprising the invention.

More particularly, the respiratory gas spectrometer is initially calibrated upon production at the factory to ensure that detected radiation intensity values will provide a basis to accurately determine the concentration of the predetermined components of interest within the gas sample (e.g., via statistical processing techniques, including partial least squares analysis). Such predetermined gas components may include oxygen, $CO_2$, and/or one or more anesthetic agents such as nitrous oxide, halothane, enflurane, and isoflurane. In conjunction with calibration, a calibration condition procedure is initiated according to a predetermined/preprogrammed protocol, wherein the reference gas chamber is open to or otherwise provided with a predetermined reference gas and the sample gas chamber is purged with a predetermined reference gas (e.g., ambient/factory air with $CO_2$ removed). Radiation beams are then alternately provided on each of the first and second optical pathways. In turn, one or more corresponding first and second calibration condition values are obtained via output from the detector array (e.g., measured at one or more centered wavelengths). Such values are then stored in the memory device, preferably in a non-volatile memory component thereof.

Subsequently, e.g. after the gas spectrometer has been put into use, a test procedure utilizing the above-noted predetermined/preprogrammed protocol can be carried out in accordance with the present invention. More particularly, such test procedure may be initiated by a user via input at the user interface (e.g., input via a keyboard or cursor). Alternatively, the processor/controller may be preprogrammed to automatically initiate such test procedure during a period of nonuse and/or to otherwise automatically prompt a user via the user interface (e.g., via audible or visual alert signals) that such test procedure should be initiated. By way of example, such automatic prompting may be triggered by a clock drive interfacing with the processor/controller to prompt the user via the user interface to conduct the test procedure on a predetermined periodic basis.

Upon initiation of the test procedure, the sample gas chamber is purged with a reference gas (e.g. ambient air with $CO_2$ removed), wherein each of the reference and gas sample chambers contain a reference gas as per the initial calibration noted above. First and second test radiation beams are then alternately provided on the first and second optical pathways and one or more first test condition values and one or more second test condition values are obtained via output from the detector array; again, utilizing the predetermined/preprogrammed protocol also employed in the calibration condition procedure noted above. Comparison of the stored first and second calibration values with the first and second test values can then be carried out to provide user feedback as noted above.

As can be appreciated, the processor/controller can be preprogrammed to automatically disable the spectrometer in the event test procedures are not carried out on the predetermined basis or when a test procedure indicates that the condition of the spectrometer is outside of predetermined tolerance values relative to the desired calibration condition.

DETAILED DESCRIPTION

Figure 1:
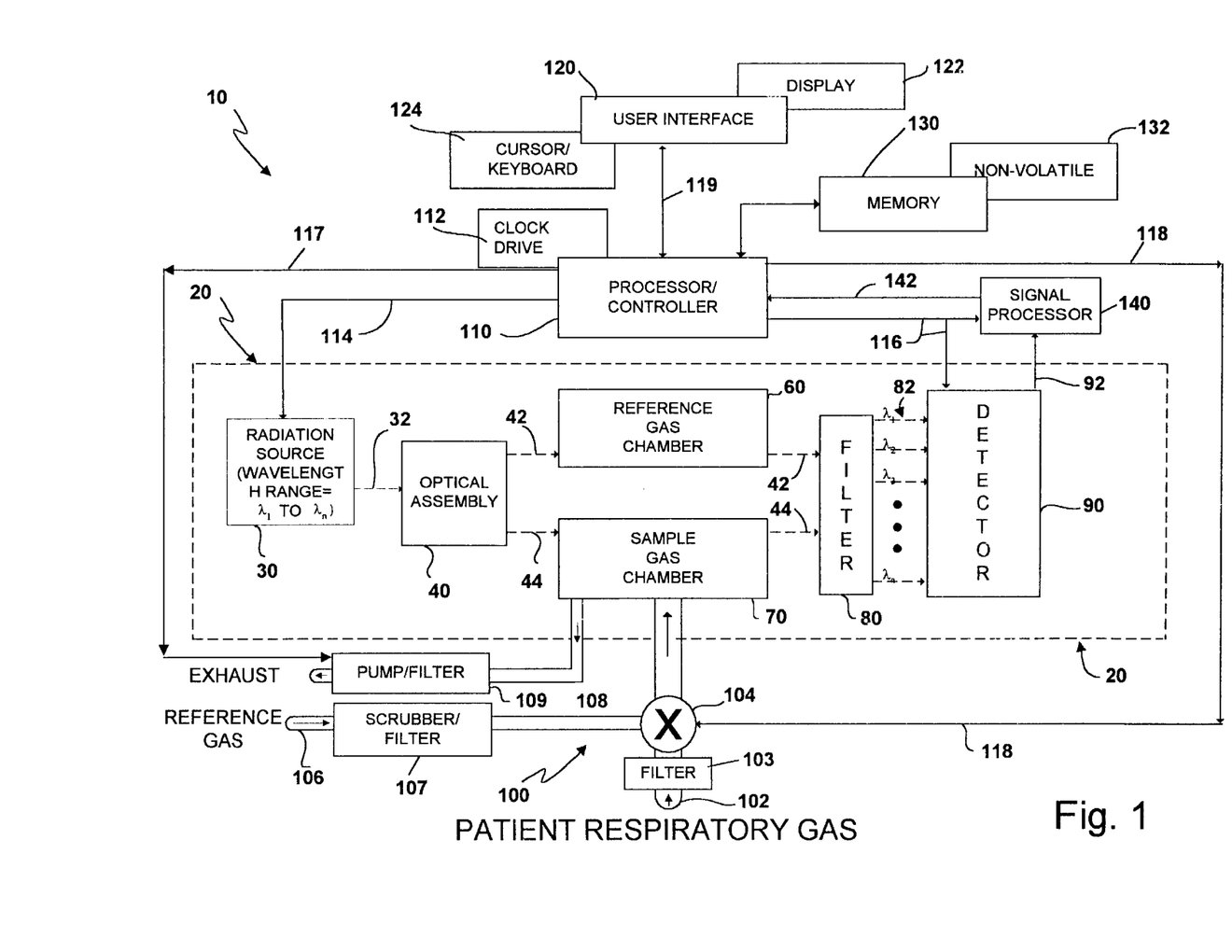
FIG. 1 is a schematic illustration of a respiratory gas spectrometer embodiment of the present invention.
Figure 2:
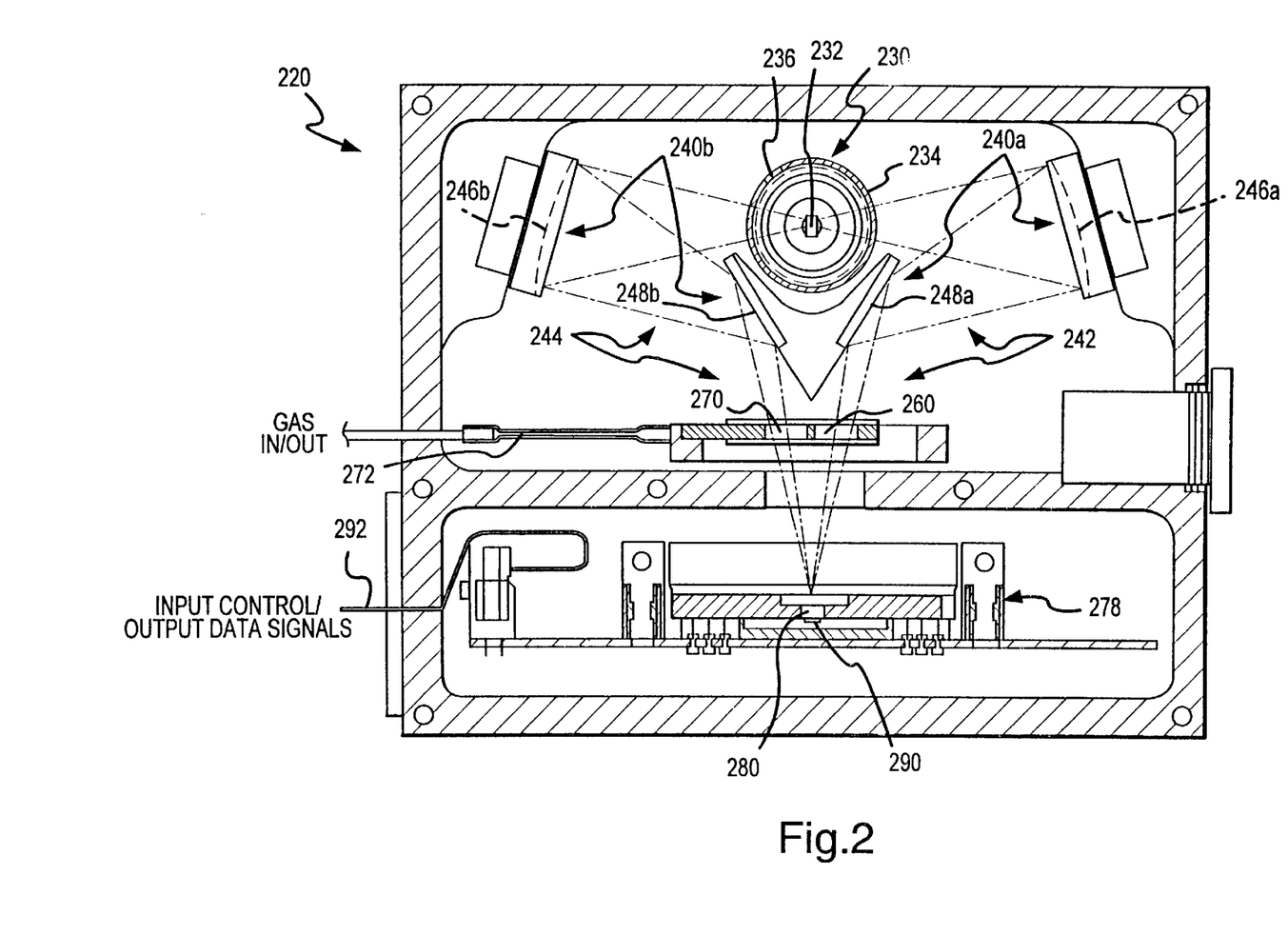
FIG. 2 is a top, cross section view of one optical bench assembly that may be utilized in the embodiment of FIG. 1.
Figure 3A:
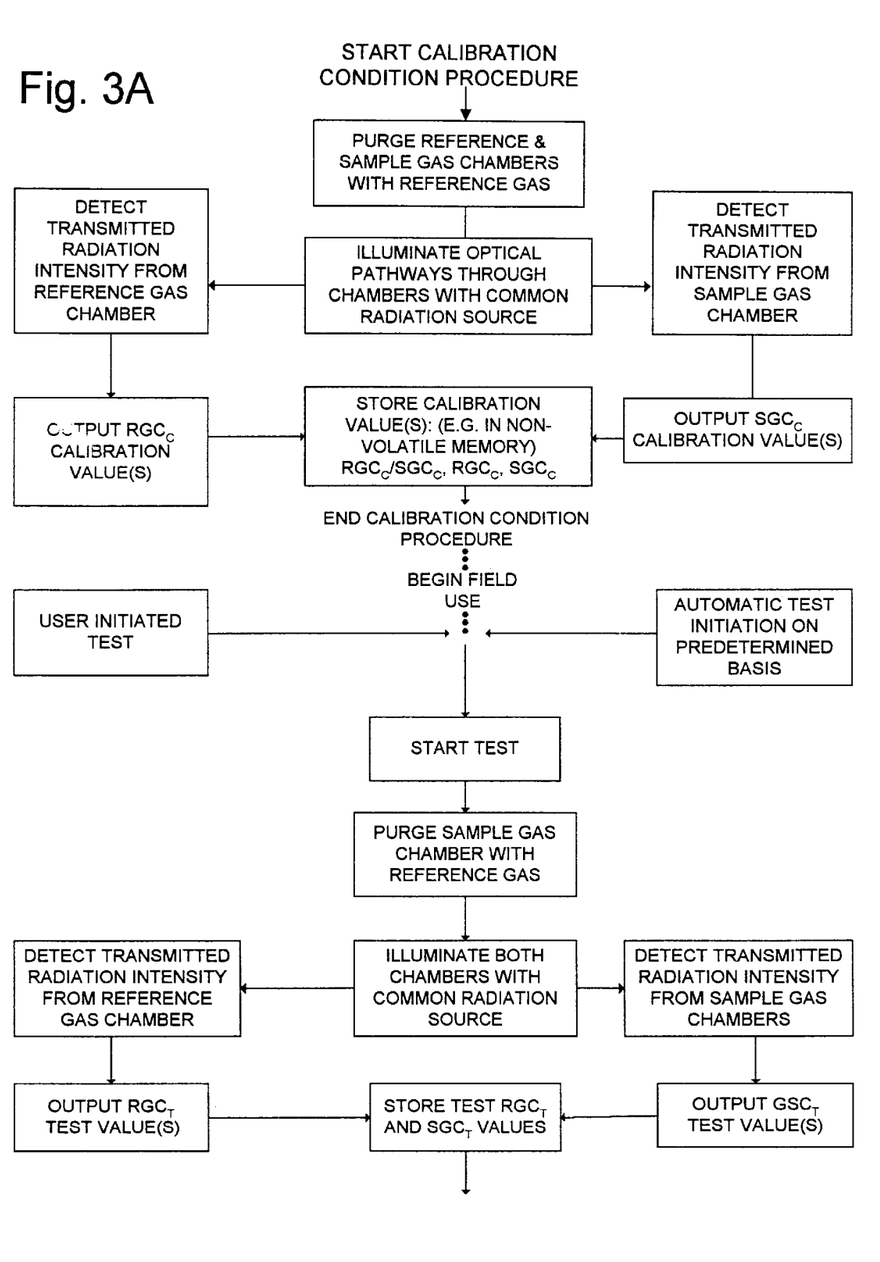
FIGS. 3A and 3B are a process flow diagram for the embodiment of FIG. 1.
Figure 3B:
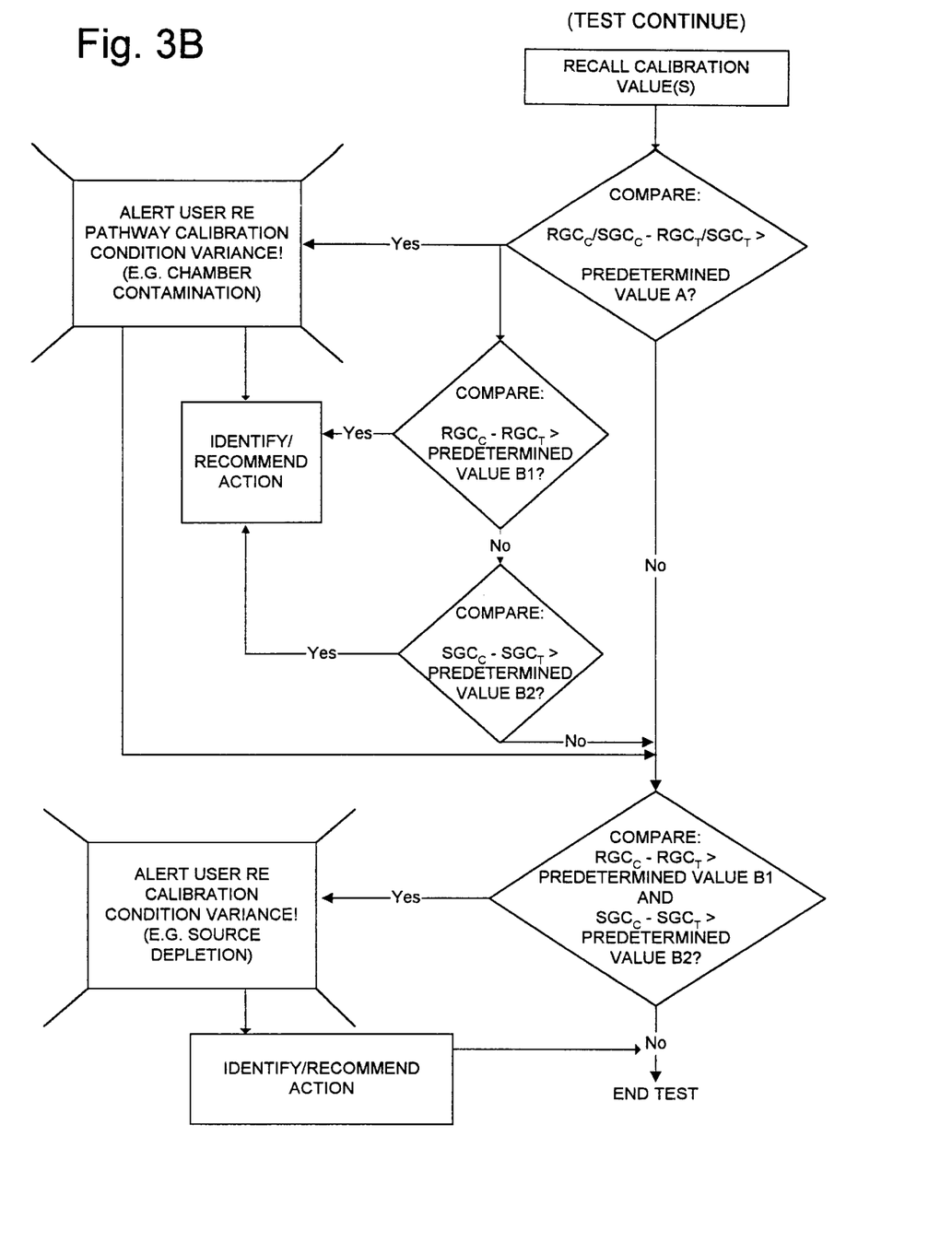

FIGS. 1–3 pertain to a respiratory gas spectrometer embodiment 10 of the present invention. The respiratory gas spectrometer 10 includes an optical bench assembly 20, a gas handling assembly 100 for transferring gases to/from the optical bench assembly 20, and a processor/controller 110 interconnected to a user interface 120, memory 130, and signal processor 140 for controlling operations and processing information within the spectrometer 10. As will be appreciated, the various described components may be disposed within a transportable housing (not shown) positionable adjacent to a patient who has received or is receiving an anesthetic gas and whose respiratory inhalations and exhalations are being monitored. More generally, the present invention may be readily utilized in a respiratory gas spectrometer as disclosed in U.S. patent application Ser. No. 08/403,161, hereby incorporated by reference in its entirety.

As illustrated in FIG. 1, the optical bench assembly 20 includes a radiation source 30 for providing radiation 32 across a predetermined wavelength range (e.g. $\lambda_1$–$\lambda_n$) to optical assembly 40. In turn, optical assembly 40 provides first and second radiation beams 42 and 44 on corresponding optical pathways passing through a reference gas chamber 60 and sample gas chamber 70, respectively. Radiation comprising the first and second radiation beams 42 and 44 which is transmitted through reference gas and sample chambers 60 and 70 respectively, impinges upon a radiation filter 80. As will be appreciated, the transmitted radiation can be employed to determine the concentration of, one or more predetermined components of a gas sample contained in sample gas chamber 70 utilizing known spectral absorption characteristics of the components across the predetermined wavelength range of the radiation beams. In this regard, filter 80 may provide for spatial filtering across at least a portion of the predetermined wavelength range that corresponds with wavelength bands within which selected anesthetic gases display unique absorbance characteristics. The filtered radiation 82 is received by a detector 90. Detector 90 may comprise an array of radiation-sensitive elements each positioned to receive radiation at a predetermined, center-wavelength (i.e. $\lambda_1-\lambda_n$) distributed across the predetermined wavelength range.

Detector 90 provides an output signal 92 reflective of the intensity of the radiation received by the various radiation-sensitive elements at their corresponding center-wavelengths ($\lambda_1-\lambda_n$). Signal 92 is processed by a signal processor 140 (e.g., comprising analog-to-digital/ amplification circuitry), and signal processor 140 outputs digital signal 142 to processor/controller 110. As will be further described, the optical bench assembly 20 and other noted components may be employed in the present invention to establish calibration condition values (e.g. upon production) and to obtain corresponding test condition values (e.g. during field use) employable to monitor the desired maintenance of the calibrated condition of the spectrometer.

In field use of the spectrometer 10, the processor/ controller 110 utilizes data provided by digital signal 142 and preprogrammed, statistical processing algorithms stored/recalled from memory 130 (e.g. in nonvolatile storage portion 132) to determine the concentration of one or more anesthetic agents, carbon dioxide and/or oxygen in the gas stream provided to sample gas chamber 70 via patient respiratory gas line 102 and filter 103 (e.g. to remove mucus, etc.). In turn, such concentration(s) are monitored by processor/controller 110 according to a predetermined protocol, wherein a variation(s) in such concentration(s) beyond a predetermined tolerance level causes user interface 120 to alert a user (e.g. via a display 122). In order to coordinate operation of the radiation source 30, readout from detector 90 and processing by signal processor 140, a clock drive 112 interfaces with processor/controller 110 to provide clocked control signals 114 and 116.

As indicated, processor/controller 110, user interface 120 and memory 130 may be employed together with optical bench assembly 20 to monitor the maintenance of a desired calibrated condition of spectrometer 10. Such monitoring is of particular benefit in respiratory gas applications which require a high degree of responsiveness and accuracy.

In this regard, and by way of example, FIG. 2 illustrates an optical bench assembly 220 that is particularly apt for respiratory gas applications since it provides for the simultaneous obtainment of measured intensity values at a plurality of center-wavelengths, such plurality being greater than the number of anesthetic gas agents for which concentrations are to be measured so as to provide an overdetermined system. More particularly, optical bench assembly 220 includes a radiation source 230 having a elongated, upstanding infrared source element 232 and a cylindrical, concentrically disposed chopper 234. Chopper 234 includes a window 236 and is rotatable (e.g. via a motor drive about the source element 232 for alternately transmitting radiation towards first and second optical assemblies 240*a* and 240*b*. It will be appreciated, the processor/controller (not shown in FIG. 3) may provide control signals to a motor (not shown) for rotating chopper 234. The first and second optical assemblies 240*a* and 240*b*, include first and second spherical mirrors 246*a* and 246*b*, and first and second flat mirrors 248*a* and 248*b*, respectively, for collecting and directing radiation to provide first and second optical beams 242 and 244, respectively. A reference gas chamber 260 and sample gas chamber 270 are disposed, relative to the optical assemblies 240*a* and 240*b*, such that the first beam 242 passes through the reference gas chamber 260 and the second beam 244 passes through the sample gas chamber 270. As illustrated, gas flow lines 272 are provided to cycle gas to/from the chamber 270, and more particularly, to cycle a sample stream of respiratory gas from a patient through the sample gas chamber 270 during use.

A detector assembly 278 includes an upstanding, linear-variable filter 280, and adjacent bandpass filter (not shown) positioned therebelow. An upstanding, linear array of pyroelectric or thermo-coupled detector elements 290 is positioned behind linear variable filter 280 and bandpass filter. The detector assembly 278 is positioned so that radiation transmitted through chambers 260 and 270 is filtered by linear variable filter 280 and the bandpass filter, then detected by the linear detector array 290. More particularly, the linear variable filter 280 may be advantageously selected to filter radiation in a spatially distributed manner across the 7–10 micron range. As will be appreciated, the 7–10 micron range covers sub-ranges across which many anesthetic gas agents display unique radiation absorbance characteristics. The bandpass filter can be selected to pass radiation in the 4–5 micron range, which range encompasses that within which $CO_2$ displays unique radiation absorbance characteristics. By utilizing detector array 290 to obtain intensity measurement values across the 7–10 and 4–5 micron wavelength ranges, the resultant data provided by detector output 292 can be provided to a processor/controller (not shown) for multi-variate statistical processing. In turn, the concentration of one or more anesthetic gas agents, oxygen and $CO_2$ can be determined and output to a user (e.g. via display 122).

Referring now to FIGS. 3A and 3B, as well as FIG. 1, operation of one embodiment of the present invention will be discussed. Specifically, upon initial calibration of respiratory gas spectrometer 10 (i.e. to ensure that measured intensity values will result in accurate concentration determinations), a calibration condition procedure is initiated. In this regard, the sample gas chamber 70 is purged with a predetermined reference gas (e.g., ambient air with $CO_2$ removed via scrubber/filter 107). In this regard, processor/ controller 110 may provide a control signal 118 to valve 104 of the gas transfer assembly 100 and control signal 117 to pump 109 so as to draw a reference gas through line 106 and scrubber/filter 107 and into sample gas chamber 70. Reference gas chamber 60 may also be initially open to or otherwise provided with a reference gas during calibration procedures. Processor/controller 110 then provides control signal 114 to the radiation source 30 (e.g. to a motor for driving chopper 234 in FIG. 2), wherein first and second radiation beams 42 and 44 illuminate corresponding optical pathways passing through reference gas chamber 60 sample gas chamber 70, respectively. The first and second reference radiation beams 42 and 44 transmitted by the reference gas chamber 60 and sample gas chamber 70, respectively, are received by filter 80 and the intensity of the resultant filtered radiation 82 at a plurality of center-wavelengths (i.e. $\lambda_1-\lambda_n$) is detected by detector 90. In response, detector 90 outputs one or more reference gas chamber calibration value(s) $RGC_c$ and one or more sample gas chamber calibration value(s) $SGC_c$, which calibration value(s) are stored at memory 130 (e.g. in non-volatile memory 132) for recall by processor/controller 110. Further, the $RGC_c$ and $SGC_c$ values may be utilized by processor/controller to generate additional values, e.g. an $RGC_c/SGC_c$ ratio value(s), which is also stored in memory 130.

Subsequently, e.g. after the spectrometer is put into field use, test procedures may be conducted periodically in order to monitor and otherwise insure the maintenance of calibration conditions. Such test procedures may be user-initiated utilizing user interface 120 (e.g. via cursor/keyboard 124) to trigger a test procedure via processor/controller 110. Alternatively, the test procedure may be automatically initiated on a predetermined basis (e.g. at predetermined time periods during periods of nonuse). As will be appreciated, test procedure operations may be preprogrammed for execution/control by processor/controller 110.

Upon initiation of the test procedure, processor/controller 110 may provide control signals 118 to valve 104 and control signals 117 to pump/filter 109 so as to draw a predetermined reference gas (e.g. ambient air) through line 106, scrubber/filter 107 (e.g. to remove $CO_2$) and into sample gas chamber 70. Processor/controller 110 may also provide control signal 114 to the radiation source 30 (e.g. to a motor for driving chopper 234 in FIG. 3), wherein first and second test radiation beams 42 and 44 are provided to illuminate corresponding optical pathways through the reference gas chamber 60 and sample gas chamber 70, respectively. The first and second test radiation beams 42 and 44 transmitted by the reference gas chamber 60 and sample gas chamber 70, respectively, are received by filter 80 and the intensity of the filtered radiation 82 is detected by detector 90 at a plurality of wavelengths (i.e. $\lambda_1-\lambda_n$). In response, detector 90 outputs one or more reference gas chamber test value(s) $RGC_t$ in one or more sample gas chamber test value(s) $SGC_t$. The $RGC_t$ and $SGC_t$ values are then stored in memory 130 (e.g. in a nonvolatile portion 132). Additionally, $RGC_t$ and $SGC_t$ values may be utilized by processor/controller 110 to generate additional values e.g., an $RGC_t/SGC_t$ ratio value(s), which are also stored at memory 130.

The stored $RGC_c$ and $SGC_c$ values, and corresponding $RGC_t$ and $SGC_t$ values are then recalled for processing in accordance with preprogrammed instructions by processor/controller 110. For example, the ratio of $RGC_c/SGC_c$ may be compared with the ratio of $RGC_t/SGC_t$. If the difference therebetween exceeds a predetermined value (i.e. representing an acceptable operational tolerance value), the user may be alerted (e.g. on display 122 of user interface 120 responsive to a control signal 119 from processor/controller 110) as to a calibration condition variance. In particular, for example, a difference between the above-noted ratios indicates that one of the pathways corresponding with either the first or second radiation beams 42 and 44 has varied from the desired calibration condition. Such variation may be caused by contamination accumulation on the windows of gas sample chamber 70 and/or variations in optical assembly 70 (e.g. misalignment of or surface contamination on components of the optical assembly 40). In this regard, further comparisons may be made between $RGC_c$ and $RGC_t$ (i.e. to determine if the difference therebetween exceeds a predetermined tolerance value $B_1$) and between $SGC_c$ and $SGC_t$ (i.e. to determine whether the difference therebetween exceeds a predetermined tolerance value $B_2$) to determine which of the optical paths has undergone a calibration condition variation. Based on preprogrammed instructions, processor/controller 110 may also identify and/or recommend actions to a user via user interface 120 (e.g. notifying the user that the device should be serviced, before further use, etc.).

In addition to the above-noted comparisons, the test procedure may provide for further comparison of $RGC_c$ and $RGC_t$ and for further comparison of $SGC_c$ and $SGC_t$. If such comparisons indicate variations greater than the corresponding predetermined values $B_1$ and $B_2$, respectively, a further calibration condition variance can be indicated. Specifically, if both of such comparisons indicate a variation beyond the corresponding predetermined tolerance value, this would indicate that the infrared source 30 has been depleted to the point that the attainment of the desired signal-to-noise ratio at detector 90 is in jeopardy. As a result, processor/controller 110 may again identify or recommend a specific action via user interface 120 (e.g. return of the device for servicing and/or replacement of the infrared source 30, etc.).

As will be appreciated, numerous embodiments, modifications and applications will exist for implementation of the current invention. Such embodiments, modifications and applications are within the scope of the present invention as defined by the claims which follow.

What is claimed is:

1. A method for monitoring maintenance of a desired calibration condition of a respiratory gas spectrometer for measuring the concentration of one or more predetermined components in respiratory gas samples, comprising:

first providing first and second calibration radiation beams on corresponding first and second optical pathways, said first optical pathway passing through a corresponding first containment area of said spectrometer and said second optical pathway passing outside said first containment area, and said spectrometer being in a desired calibration condition;

first detecting an intensity of said first calibration radiation beam passing through the first containment area, and an intensity of the second calibration radiation beam passing outside of the first containment area, to obtain corresponding first and second calibration condition values;

placing the spectrometer into use to measure the concentration of one or more predetermined components of respiratory gas samples;

second providing first and second test radiation beams on said corresponding first and second optical pathways, said first optical pathway passing through the corresponding first containment area of said spectrometer and said second optical pathway passing outside said first containment area, and said spectrometer being in an in-use condition;

second detecting an intensity of said first and second test radiation beams to obtain corresponding first and second test condition values; and using said first and second calibration condition values and said first and second test condition values to monitor an in-use condition of the gas spectrometer in relation to said desired calibration condition.

2. A method as recited in claim 1, said placing step comprising:

containing said respiratory gas samples in said first containment area as defined by a sample gas chamber.

3. A method as recited in claim 2, said first providing and second providing steps each comprising:

purging said sample gas chamber to remove gaseous components corresponding with said one or more predetermined components of respiratory gas samples.

4. A method as recited in claim 3, wherein said second optical pathway passes through a corresponding second containment area as defined by a reference gas chamber, and wherein in said first providing and second providing steps said reference gas chamber is substantially free of said one or more predetermined components to be measured in said respiratory gas samples.

5. A method as recited in claim 1, said using step comprising:
   generating a first value utilizing said first and second calibration condition values;
   generating a second value utilizing said first and second test condition values;
   comparing said first and second values to determine whether a difference therebetween exceeds a predetermined value.

6. A method as recited in claim 5, wherein when said difference is greater than said predetermined value, said method further comprises:
   alerting a user that a variation from said desired calibration condition exists.

7. A method as recited in claim 6, wherein said variation comprises contamination in a sample gas chamber defining said first containment area, said sample gas chamber being employed for containing said respiratory gas samples during said placing step.

8. A method for monitoring maintenance of a desired calibration condition of a respiratory gas spectrometer for measuring the concentration of one or more predetermined components in respiratory gas samples, comprising:
   first providing first and second calibration radiation beams on corresponding first and second optical pathways, said first optical pathway passing through a corresponding first containment area of said spectrometer, and said spectrometer being in a desired calibration condition;
   first detecting an intensity of said first and second calibration radiation beams to obtain corresponding first and second calibration condition values;
   placing the spectrometer into use to measure the concentration of one or more predetermined components of respiratory gas samples;
   second providing first and second test radiation beams on said corresponding first and second optical pathways, said first optical pathway passing through the corresponding first containment area of said spectrometer, and said spectrometer being in an in-use condition;
   second detecting an intensity of said first and second test radiation beams to obtain corresponding first and second test condition values; and
   using said first and second calibration condition values and said first and second test condition values to monitor an in-use condition of the gas spectrometer in relation to said desired calibration condition, said using step comprising:
      comparing said first calibration condition value and said first test condition value to determine whether a difference therebetween exceeds a first predetermined value;
      comparing said second calibration condition value and said second test condition value to determine whether a difference therebetween exceeds a second predetermined value;
      alerting a user that variation from said calibration condition exists when both of said first and second predetermined values are exceeded.

9. A method as recited in claim 8, wherein said variation comprises depletion of a radiation source utilized to generate said first and second reference radiation beams and said first and second test radiation beams.

10. A respiratory gas spectrometer comprising:
    an infrared radiation source;
    an optical assembly for receiving infrared radiation from the source and directing said infrared radiation on first and second optical paths;
    a sample gas chamber positioned on the first optical path and positioned so that the second optical path passes outside of the sample gas chamber;
    a detector for detecting an intensity of the infrared radiation passing through the sample gas chamber on the first optical path, for detecting an intensity of the infrared radiation on the second optical path passing outside of the sample gas chamber, and for providing corresponding first and second outputs;
    a memory device for storing calibration condition information established using said first and second outputs with the gas spectrometer in a desired calibration condition; and
    a comparator for comparing said stored calibration condition information with in-use condition information established using the first and second outputs with the gas spectrometer in an in-use condition, wherein the in-use condition is monitored in relation to the desired calibration condition.

11. A respiratory gas spectrometer as recited in claim 10, said memory device comprising a non-volatile memory for storing said calibration condition information.

12. A respiratory gas spectrometer as recited in claim 10, further comprising:
    a processor for controlling the obtainment of said in-use information according to preprogrammed instructions.

13. A respiratory gas spectrometer as recited in claim 10, further comprising:
    a user interface for alerting a user when said in-use condition varies in relation to said desired calibration condition by greater than a predetermined value.

14. A respiratory gas spectrometer as recited in claim 10, further comprising:
    a reference gas chamber positioned on the second optical path.

15. A method for monitoring maintenance of a desired calibration condition of a respiratory gas spectrometer for measuring the concentration of one or more predetermined components respiratory gas samples, comprising:
    first providing first and second calibration radiation beams on corresponding first and second optical pathways, said first optical pathway passing through a sample gas chamber, wherein said sample gas chamber is purged to remove gaseous components corresponding with said one or more predetermined components, said second optical pathway passing through a reference gas chamber, and said spectrometer being in a desired calibration condition;
    first detecting an intensity of said first and second calibration radiation beams to obtain corresponding first and second calibration values;
    placing the spectrometer into use to measure the concentration of one or more predetermined components of respiratory gas samples, said respiratory gas samples being contained in said sample gas chamber;
    second providing first and second test radiation beams on said corresponding first and second optical pathways, said first optical pathway passing through said sample gas chamber, wherein said sample gas chamber is purged to remove gaseous components corresponding with said one or more predetermined components, said second optical pathway passing through said reference gas chamber, and said spectrometer being in an in-use condition;

second detecting an intensity of said first and second test radiation beams to obtain corresponding first and second test condition values; and using said first and second calibration condition values and said first and second test condition values to monitor an in-use condition of the gas spectrometer in relation to said desired calibration condition.

16. A method as recited in claim 15, said using step comprising generating a first value utilizing said first and second calibration condition values;

generating a second value utilizing said first and second test condition values;

comparing said first and second values to determine whether a difference therebetween exceeds a predetermined value.

17. A method as recited in claim 16, wherein when said difference is greater than said predetermined value, said method further comprises:

alerting a user that a variation from said desired calibration condition exists.

18. A method as recited in claim 17, wherein said variation comprises contamination in a sample gas chamber defining said first containment area, said sample gas chamber being employed for containing said respiratory gas samples during said placing step.

* * * * *